United States Patent [19]
Andreas et al.

[11] Patent Number: 5,797,929
[45] Date of Patent: Aug. 25, 1998

[54] APPARATUS AND METHODS FOR ADVANCING SURGICAL KNOTS

[75] Inventors: Bernard H. Andreas, Fremont; Timothy J. Wood, Santa Clara, both of Calif.

[73] Assignee: Perclose, Inc., Menlo Park, Calif.

[21] Appl. No.: 552,211

[22] Filed: Nov. 2, 1995

Related U.S. Application Data

[63] Continuation of Ser. No. 252,310, Jun. 1, 1994, abandoned.

[51] Int. Cl.⁶ .................................................. A61B 17/00
[52] U.S. Cl. ........................ 606/148; 606/139; 606/144
[58] Field of Search ........................... 606/139, 144–146, 606/148; 289/17

[56] References Cited

U.S. PATENT DOCUMENTS

| | | | |
|---|---|---|---|
| 1,574,362 | 2/1926 | Callahan . | |
| 1,940,351 | 12/1933 | Howard . | |
| 2,131,321 | 9/1938 | Hart . | |
| 2,595,086 | 4/1952 | Larzelere . | |
| 3,131,957 | 5/1964 | Musto | 289/17 |
| 3,625,556 | 12/1971 | Stromberg | 289/17 |
| 3,898,992 | 8/1975 | Balamuth | 606/144 |
| 4,803,984 | 2/1989 | Narayanan et al. . | |
| 5,084,058 | 1/1992 | Li | 606/148 |
| 5,147,373 | 9/1992 | Ferzli | 606/148 |
| 5,176,691 | 1/1993 | Pierce | 606/148 |
| 5,201,744 | 4/1993 | Jones | 606/148 |
| 5,234,443 | 8/1993 | Phan et al. | 606/148 |
| 5,234,444 | 8/1993 | Christoudias | 606/148 |
| 5,242,459 | 9/1993 | Buelna | 606/139 X |
| 5,250,054 | 10/1993 | Li | 606/148 |
| 5,292,327 | 3/1994 | Dodd et al. | 606/148 |
| 5,320,652 | 6/1994 | Heidmueller | 606/144 |
| 5,324,298 | 6/1994 | Phillips et al. | 606/148 |
| 5,342,374 | 8/1994 | Wan et al. | 606/148 |

FOREIGN PATENT DOCUMENTS

| | | | |
|---|---|---|---|
| 820810 | 6/1979 | U.S.S.R. | 606/148 |

*Primary Examiner*—Michael Peffley
*Attorney, Agent, or Firm*—Townsend and Townsend and Crew LLP

[57] ABSTRACT

A knot pusher comprises a shaft having a fitting at its distal end. The fitting includes a radial slot for receiving a suture length therein. A mechanism is provided for closing the slot so that the suture can be contained within the slot as a knot is advanced over the contained suture length.

23 Claims, 8 Drawing Sheets

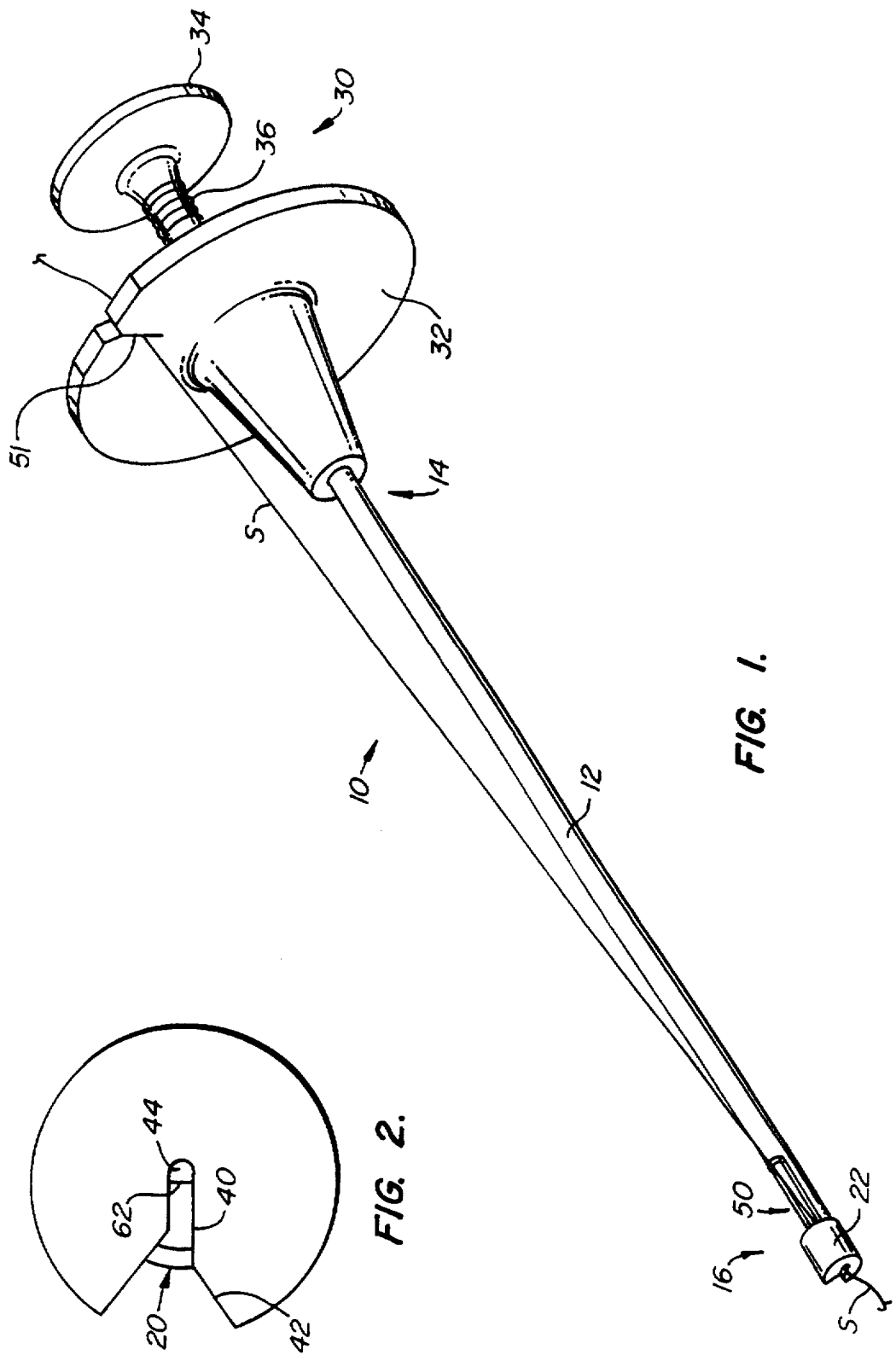

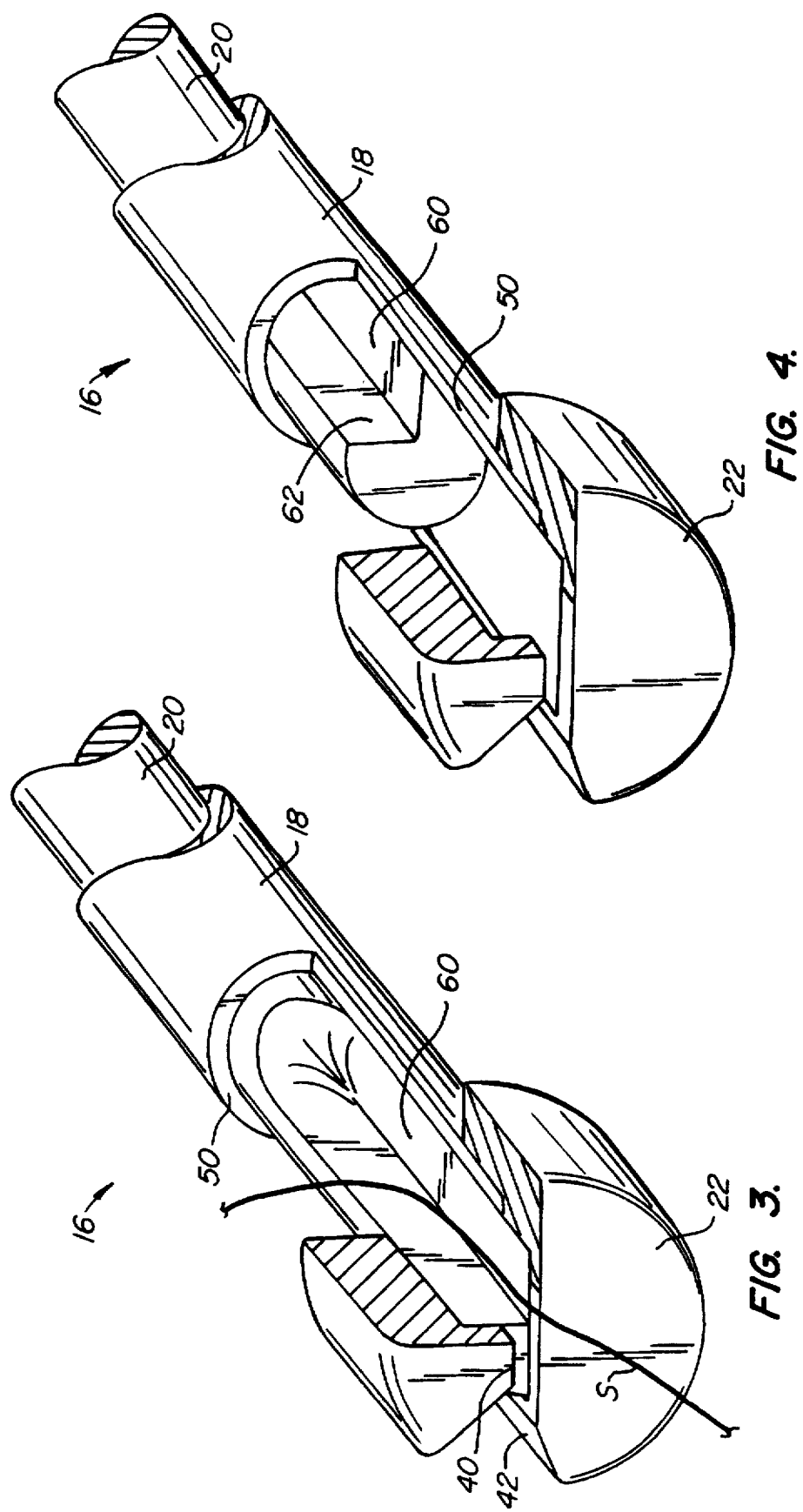

5,797,929

1
APPARATUS AND METHODS FOR ADVANCING SURGICAL KNOTS

This is a Continuation of U.S. application Ser. No. 08/252,310, filed Jun. 1, 1994 (now abandoned).

BACKGROUND OF THE INVENTION

1. Field of the Invention

The present invention relates generally to surgical devices and methods. More particularly, the present invention relates to the construction and use of devices for advancing surgical knots, commonly referred to as "knot pushers."

The closing of incisions and wounds using sutures is a preferred technique of surgeons and many other physicians. While other techniques are now available, such as stapling, the use of "tissue glues," and the use of collagen for closing vascular puncture, the use of suture is often preferred since it provides a reliable and tight closure of any wound where the suture can be properly placed, tied, and tightened.

While suturing is relatively straightforward in most open surgical procedures, placement and tying of sutures in laparoscopic and other minimally invasive procedures can be problematic. In order to provide for suturing under such circumstances, a variety of devices have been developed for the remote placement and tying of suture through cannulas under video observation. Usually, a sliding knot will be formed in a suture loop, and it will be necessary to use a tool, usually referred to as a "knot pusher," for cinching the slidable knot over the loop.

Such knot pushing devices may also be used in recently developed techniques for the remote suturing of vascular punctures. Punctures are formed in the femoral and other arteries to provide vascular access for performing angioplasty and other vascular procedures. Such techniques are described in Ser. Nos. 07/989,611 (now U.S. Pat. No. 5,417,699), 08/148,809 (now U.S. Pat. No. 5,527,322), and PCT/US93/11864. Such methods result in placement of a suture loop through tissue on opposites sides of the vascular puncture. Two free ends of the suture loop are brought out through a tissue tract leading to the puncture, and the loops may be externally tied by the treating physician. It is then necessary to use a tool to advance the knot back through the tissue tract so that it lies directly over the adventitial wall of the blood vessel.

Heretofore, knot pushers have been relatively cumbersome and awkward to employ. Frequently, one or both free ends of the suture must be threaded through an aperture or slot on the knot pusher prior to advancing the knot. The need to thread suture during the surgical procedures can be problematic and time consuming. Moreover, the suture can sometimes be lost from the open slots which are employed in many of the presently available knot pushers.

For these reasons, it would be desirable to provide improved devices and methods for advancing surgical knots where the suture can be readily loaded onto the devices and the knot advanced with a reduced chance of losing the suture. The methods and devices should be suitable for use in laparoscopic and other minimally invasive procedures, in newly developed vascular suturing protocols, as well as in open surgical and other less demanding circumstances.

2. Description of the Background Art

Knot pushers, appliers, and related suturing devices are described in U.S. Pat. Nos. 5,250,054; 5,201,744; 5,176,691; 4,803,984; 2,595,086; 2,131,321; 1,940,361; and 1,574,362.

2

Application Ser. Nos. 07/989,611 and 08/148,809, and PCT/US93/11864, describe methods and apparatus for suturing vascular punctures.

SUMMARY OF THE INVENTION

According to the present invention, an improved knot pusher device comprises a shaft having a proximal end and a distal end, wherein the distal end is configured to advance a slidable knot in a suture loop to close the loop. The distal end is usually a flat or slightly convex or concave surface having a slot for receiving a free end of a suture proximate to the knot, wherein the slot is large enough to slidably receive the free suture end but small enough to engage the knot and "push" the knot by advancing the device relative to the free suture end. The improvement comprises a capture mechanism on the distal end of the shaft to maintain the suture within the distal end while still allowing free axial travel of the suture within the slot. The slot is preferably configured to allow easy capture of the suture, even while the device is being manipulated through an access sleeve or trocar, and the capture mechanism assures that the suture will not be inadvertently lost from the slot as the knot is advanced.

An exemplary and preferred knot pusher comprises the shaft having a proximal and a distal end. A fitting is mounted on the distal end of the shaft and has a radial slot which receives the free end of suture. A member is mounted on the shaft and moves between a first position that closes the slot and a second position that leaves the slot open. In this way, by shifting the member between the two positions, the suture can be selectively captured and released as desired. The shaft is usually tubular and has a side opening located just proximally of the fitting to permit exit of the suture from the fitting. In a first design option, the member is a rod which is slidably received in a lumen of the tubular shaft, wherein the rod may be advanced to close the slot or retracted in order to open the slot. In a second design option, the member is a rotatable rod having a distal end which is shaped to close the slot in a first rotational position and to open the slot in a second rotational position.

According to a method of the present invention, a suture loop having two free ends and a slidable knot is provided at a target tissue location, such as a vascular or other incision that is to be closed and sealed. Tension is provided on a first free end of the suture loop, and the tensioned end is captured in a slot formed at the distal end of the knot pusher shaft. The slot is closed, and the shaft is advanced over the free end toward the tissue to advance the knot and close the suture loop. After the loop has been closed, the other free end of the suture loop is tensioned to tighten the knot. The slot is then opened, and the first free end of the suture loop released. The method is particularly convenient for closing and tightening suture loops located through or within percutaneous tissue punctures, such as vascular punctures to the femoral artery, trocars used in laparoscopic and other minimally invasive surgeries, and the like.

BRIEF DESCRIPTION OF THE DRAWINGS

FIG. 1 is a perspective view of a first embodiment of a knot pusher constructed in accordance with the principles of the present invention;

FIG. 2 is a distal end view of the knot pusher of FIG. 1;

FIG. 3 is a detailed perspective view of the distal end of the knot pusher of FIG. 1, shown with portions broken away and with the suture securing member in a distally extended position;

FIG. 4 is a view similar to FIG. 3, except that the suture securing member is shown in a partially retracted position;

DESCRIPTION OF THE SPECIFIC EMBODIMENTS

Figure 1A:
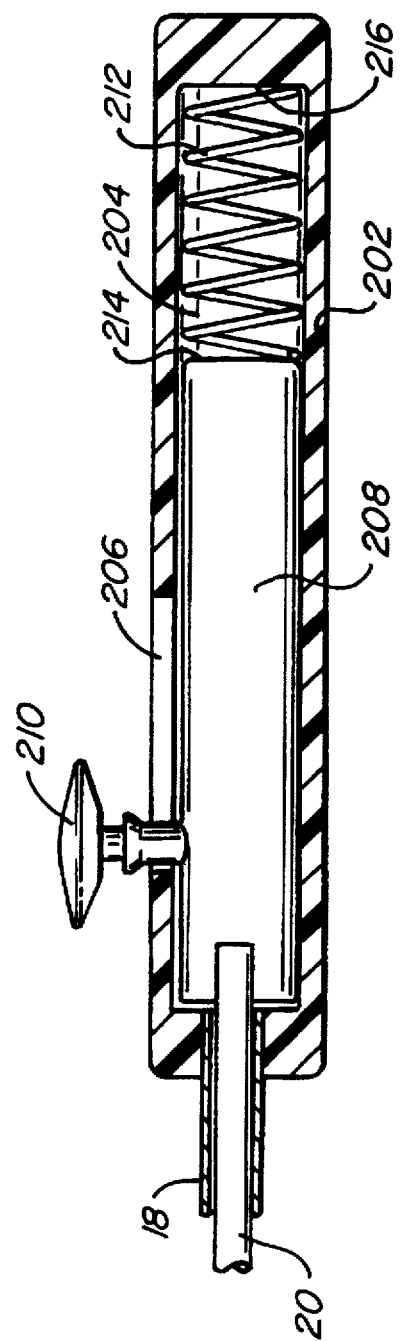
FIG. 1A is a side cross-sectional view of an alternative handle construction for the knot pusher embodiment of FIG. 1.

The knot pusher of the present invention is a manual device which can be used by physicians in any of a variety of surgical procedures where a suture loop has been formed in tissue to close an incision or wound, or for any other purpose. A slidable knot will be formed in the loop, and the knot pusher is used to engage and advance the knot over a free end of the suture to close the loop. The knot can then be tightened by pulling on the other free end of the suture, and optionally additionally throws may be tied into the suture ends and advanced using this or another knot pusher.

The knot pusher preferably comprises an elongate, narrow diameter body or shaft suitable for use in remote procedures performed through percutaneous tissue punctures, such as vascular closures, laparoscopic and other minimally invasive procedures and the like. Thus, the shaft will typically have a length in the range from about 5 cm to 40 cm, usually from about 7 cm to 10 cm. The diameter of the shaft will be sufficiently small to facilitate introduction through access sheaths, trocars, and the like, typically being below about 10 mm, preferably being in the range from 2 mm to 10 mm, and more preferably being in the range from 2 mm to 4 mm. The distal end of the shaft will be configured to engage and advance the slidable knot, and the proximal end of the shaft will typically have handles, gripping surfaces, actuators, or the like, to facilitate manual manipulation of the device. Preferably, a slit, cleat, post or other anchor is provided at the proximal end of the device to permit a temporary attachment of one or both ends of the suture during use. It will be appreciated, of course, that while the device may be particularly useful for performing remote procedures through access sheaths and trocars, it will also find use in open surgical procedures where its ability to capture suture and its one-hand operation will also provide advantages.

In a preferred aspect, a fitting will be provided at the distal end of the shaft or body of the knot pusher. The fitting will preferably be formed from a relatively hard material to firmly engage the knot and permit smooth advancement of the knot. The fitting is typically a cylindrical element having a flat (or slightly convex or concave) front face, a diameter in the range of 2 mm to 10 mm, and a length in the range from about 3 mm to 10 mm. A radial slot is formed in the fitting for receiving and capturing the suture. Preferably, the slot is flared open in the outward radial direction to facilitate capture of the suture. An opening will be provided in the shaft at the proximal end of the fitting, preferably immediately proximal to the fitting to permit exit of the captured suture from the device. Thus, the device will allow capture of the suture within the fitting, with the remaining portions of the suture lying outside of the fitting to permit tensioning, as will be described in more detail hereinafter.

The shaft or body of the knot pusher will usually be rigid, typically being formed from a medically acceptable metal or plastic material. Suitable metals include stainless steel. Suitable plastics include polycarbonate. As will be described in more detail hereinafter, the shaft may be formed from more than one component, preferably being formed from coaxial tubes or a coaxial tube and rod. The various components of the shaft may be formed from the same or different materials, but will usually be rigid metals and plastics as described above.

Referring now to FIGS. 1–4, a knot pusher 10 comprises a shaft assembly 12 having a proximal end 14 and a distal end 16. The shaft assembly 12 includes an outer tubular member 18 and an inner rod member 20, as best illustrated in FIGS. 3 and 4. A fitting 22 is mounted on the distal end 16 of shaft assembly 12 and is attached to the outer tube member 18. The rod member 20 will be axially reciprocatable within the outer tube member 18 as well as within an opening or receptacle in the proximal end of the fitting 22. The distal end of the rod member 20 is shown in its fully distally translated position in FIG. 3 and in a partially retracted position in FIG. 4.

Axial reciprocation or translation of the rod member 20 relative to the outer tube member 18 and fitting 22 is effected by an actuator assembly 30 at the proximal end 14 of the shaft assembly 12. The actuator assembly 30 includes a finger grip 32 attached to the rod member 20, and a thumb depressor 34 attached to the outer tube member 18. A spring 36 is maintained under compression between the finger grip 32 and thumb depressor 34 so that the thumb depressor (in the absence of a depression force) remains proximally retracted relative to the rod member 20. The rod member 20 can be proximally retracted by depressing the thumb depressor 34, typically by a user grasping finger grip 32 between the ring and index fingers and pressing on the depressor 34 with the thumb. It will be appreciated that a wide variety of other actuator mechanisms, such as three-ring actuators, pistol grips, thumb sliders, and the like could also be utilized in the knot pusher of the present invention.

The fitting 22 includes a radial slot 40 having a flared entrance region 42 for receiving a length of suture S as illustrated in FIG. 1. The suture S will be captured within a radially inward region 44 of the slot 40, as illustrated in FIG. 2. An opening or aperture 50 is formed in the outer tubular member 18 so that the lumen of tubular member is open to the exterior on the proximal side of the fitting 22. With this structure, it will be appreciated that suture will be able to enter the slot 40 through the flared opening 42, but will be free to exit from the lumen of tubular member 18 through opening 50. A slit 51 is provided at the proximal end of the device to permit a temporary attachment of one or both ends of the suture during use.

Capture of suture within the slot 40 is accomplished by depressing thumb depressor 34 relative to the finger grip 32 to proximally retract the interrupt member 18 and open slot 40. Such capture will, in itself, be sufficient to allow the knot pusher 10 to advance a slidable knot in the suture loop. The present invention, however, further provides a structure and mechanism for containing suture within the slot 40, as will now be described in more detail. The distal end of rod member 20 is formed with a quarter-round notch 60, as best seen in FIGS. 3 and 4. The notch 60 provides an opening for the axial passage of suture, even when the member 60 is fully advanced in the distal direction, as illustrated in FIG. 3. Wall 62 of the notch 60 is aligned with the slot 40 so that an axial passage remains in region 44. The suture S is thus able to pass through the slot 40, past the wall 62, and out through the opening 50, as best seen in FIG. 3. The wall 62, however, blocks lateral passage of the suture S through the slot 40. Thus, the suture will be maintained in the fitting 22, but will be able to axially translate through region 44 of the slot 40. The suture can be released, however, by retracting rod member 20, as illustrated in FIG. 4.

An alternative handle actuator assembly 200 for effecting axial translation of rod member 20 relative to outer tube member 18 is illustrated in FIG. 1A. The distal end of a knot pusher employing the handle actuator assembly can be identical to that illustrated in FIGS. 1–4. The handle actuator assembly 200 comprises a tubular handle casing 202 having an open interior chamber 204 and an axial slot 206 on one side thereof. A slider 208 is reciprocatably mounted in the chamber 204, and thumb knob 210 permits a user to manually slide the slider between a distally extended position (as illustrated) and a proximally retracted position (by drawing proximally on the thumb knob). Spring 212 is mounted in the chamber 204 between a proximally exposed surface 214 of the slider 208 and an internal surface 216 of the handle casing 202. The spring 212 is under slight compression so that the slider will be maintained in its distally advanced position absent proximal force on the thumb knob 210. Thus, the suture-engaging distal end of the knot pusher can be shifted between the "closed" configuration of FIG. 3 and the "open" configuration of FIG. 4 by manually retracting the thumb knob 210. That is, retraction of the thumb knob 210 is equivalent to depression of thumb depressor 34 in the embodiment of FIGS. 1–4.

Figure 6:
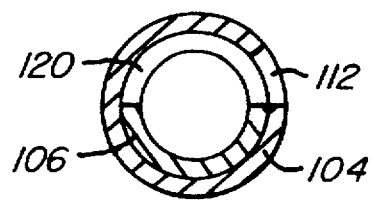
FIG. 6 is a cross-sectional view taken along the line 6—6 of FIG. 5.
Figure 6A:
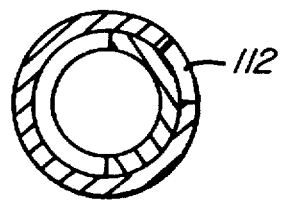
FIG. 6A is a cross-sectional view similar to FIG. 6, except that the inner tube has been rotated by 90°.
Figure 5:
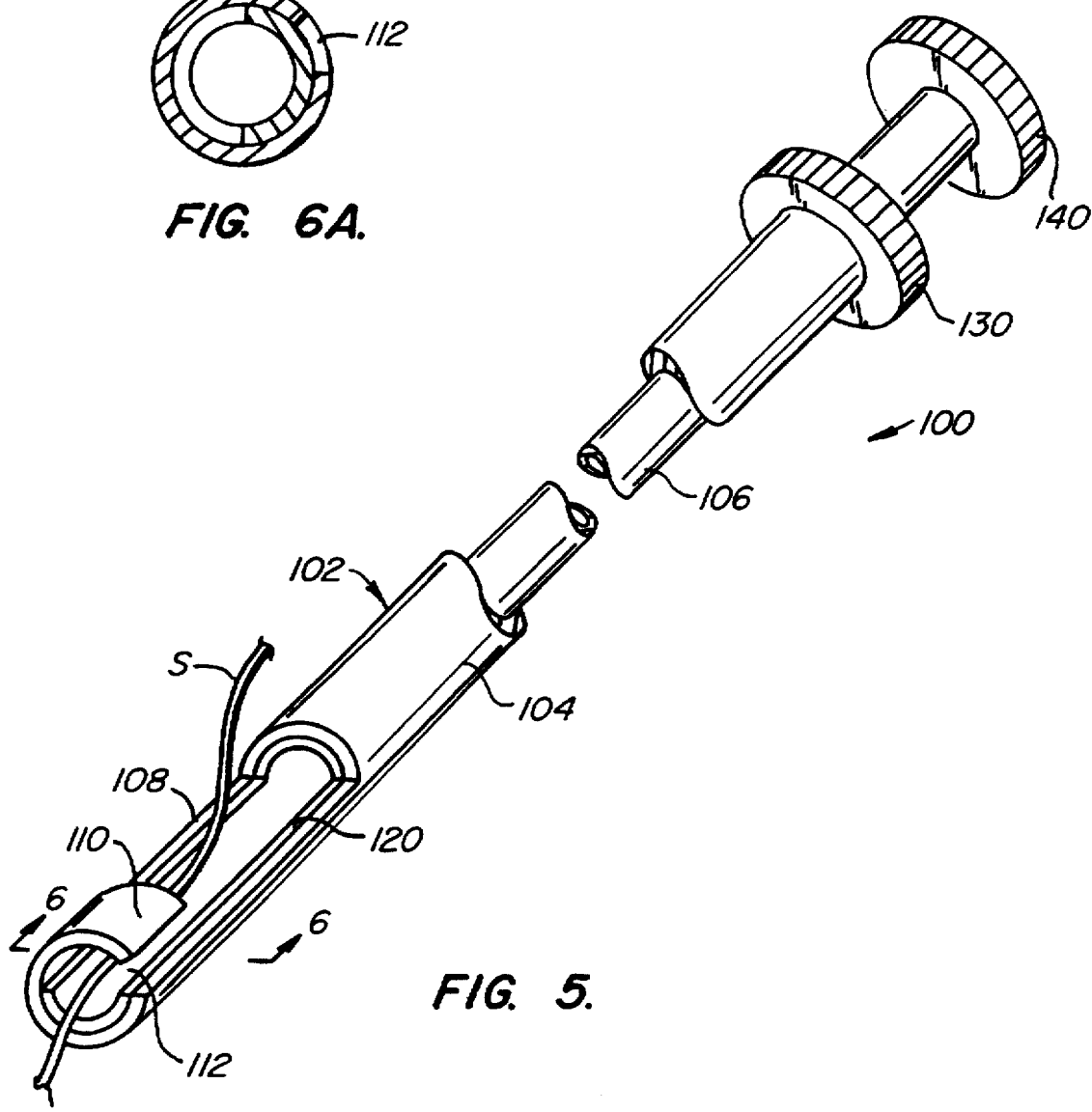
FIG. 5 is a perspective view of a second embodiment of a knot pusher constructed in accordance with the principles of the present invention.

Other mechanisms for locking the suture within a distal portion of the knot pusher may also be utilized. Referring to FIGS. 5, 6, and 6A, an alternative embodiment of a knot pusher 100 constructed in accordance with the principles of the present invention will be described. Knot pusher 100 includes a shaft assembly 102 which comprises an outer tubular member 104 and an inner tubular member 106. The outer tubular member has an opening 108 near its distal end with a C-shaped hook 110 at its distal tip. The hook element 110 defines a fitting for receiving suture through slot 112. The inner tubular member 106 also includes an opening or notch 120 at its distal end. The notch 120, however, has a semicircular profile along its entire length. Thus, when the outer tubular member 104 and inner tubular member 106 are rotationally aligned, as illustrated in FIGS. 5 and 6, the slot 112 is fully open to receive suture S as illustrated. By rotating the inner tubular member 106 by 90°, as illustrated in FIG. 6A, the slot 112 may be closed while continuing to allow free axial sliding of the suture S through the openings 108 and 120. Conveniently, knobs 130 and 140 may be provided on the proximal ends of outer tube 104 and inner tube 106, respectively, to facilitate relative rotation.

Referring now to FIGS. 7A–7E, use of the knot pusher 10 for advancing a knot K in a suture loop L to close a puncture P in a blood vessel BV will be described. Methods for placing the suture loop L so that free ends S1 and S2 of the suture pass through opposite sides of the blood vessel wall and into the percutaneous tissue tract are described in application Ser. Nos. 07/989,611; 08/148,809; and PCT/US93/11864, the full disclosures of which are incorporated herein by reference. After tying the knot K in the suture ends S1 and S2, the suture loop L will extend outward through an access sheath 150, as illustrated, and it is necessary to advance the knot K down through the lumen in sheath 150 to close the loop. The knot K, which is a slidable knot or a square knot, can then be tightened by pulling on the free ends S1 and S2.

Figure 7A:
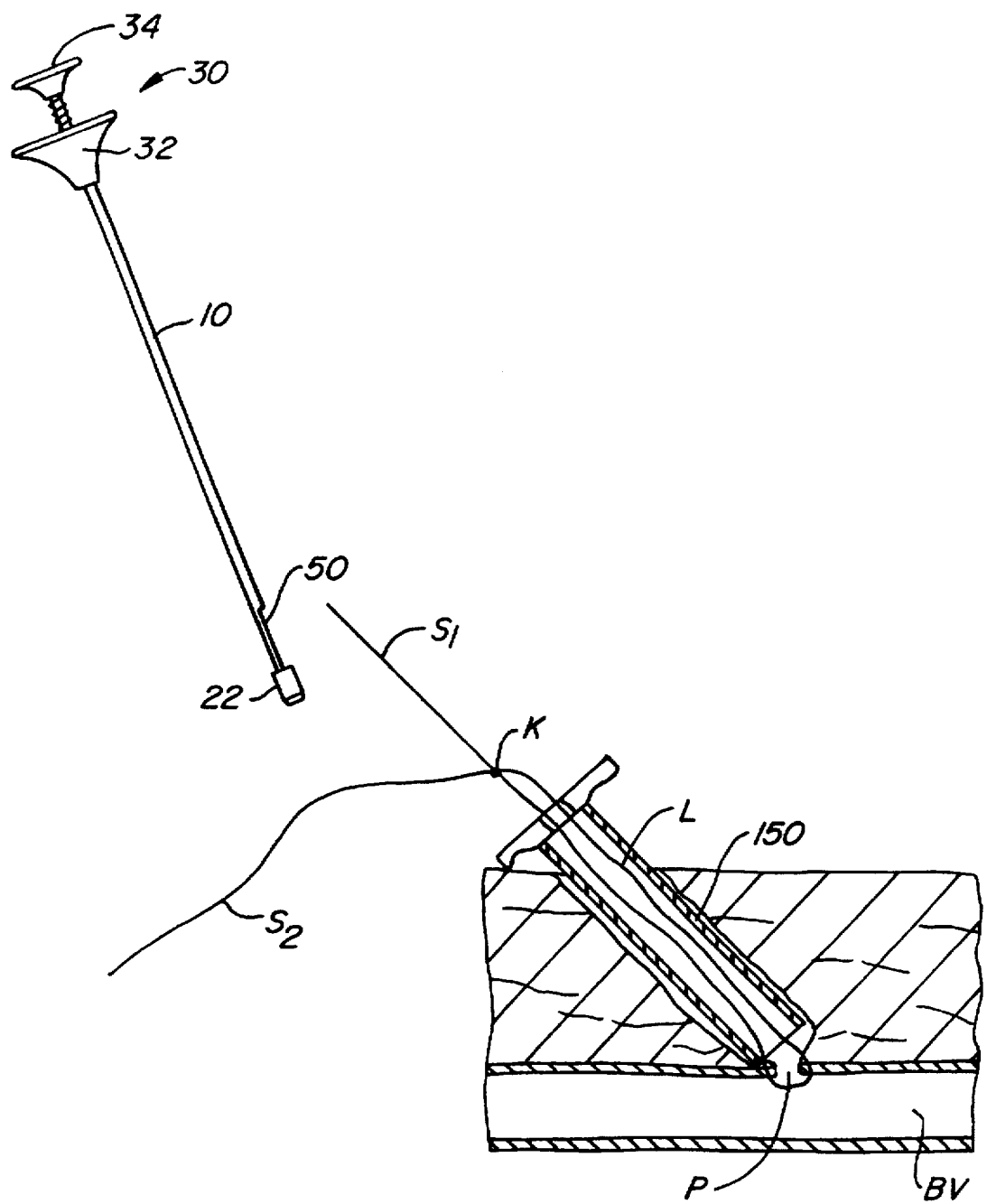
FIGS. 7A–7E illustrate the use of the knot pusher of FIG. 1 for closing and tightening a knotted suture loop through a percutaneous vascular puncture.

The method of the present invention begins by capturing a first free end S1 of the suture in the fitting 22 (FIG. 7A). The suture will be captured while the user depresses thumb depressor 34 relative to the finger grip 32 to proximally retract the inner rod member 18 and open the slot 40 (FIGS. 1–4). A particular advantage of the present invention is the ease of capturing suture through the flared entrance region 42 into slot 40 of fitting 22. The suture may simply be placed over the entrance 42 and will fall into the slot 40. Capture is completed by releasing the thumb depressor 34. After capturing the free suture end S1, the physician can use the knot pusher 10 to advance the knot K without having to depress the thumb depressor 34 until it is time to release the suture.

Figure 7B:
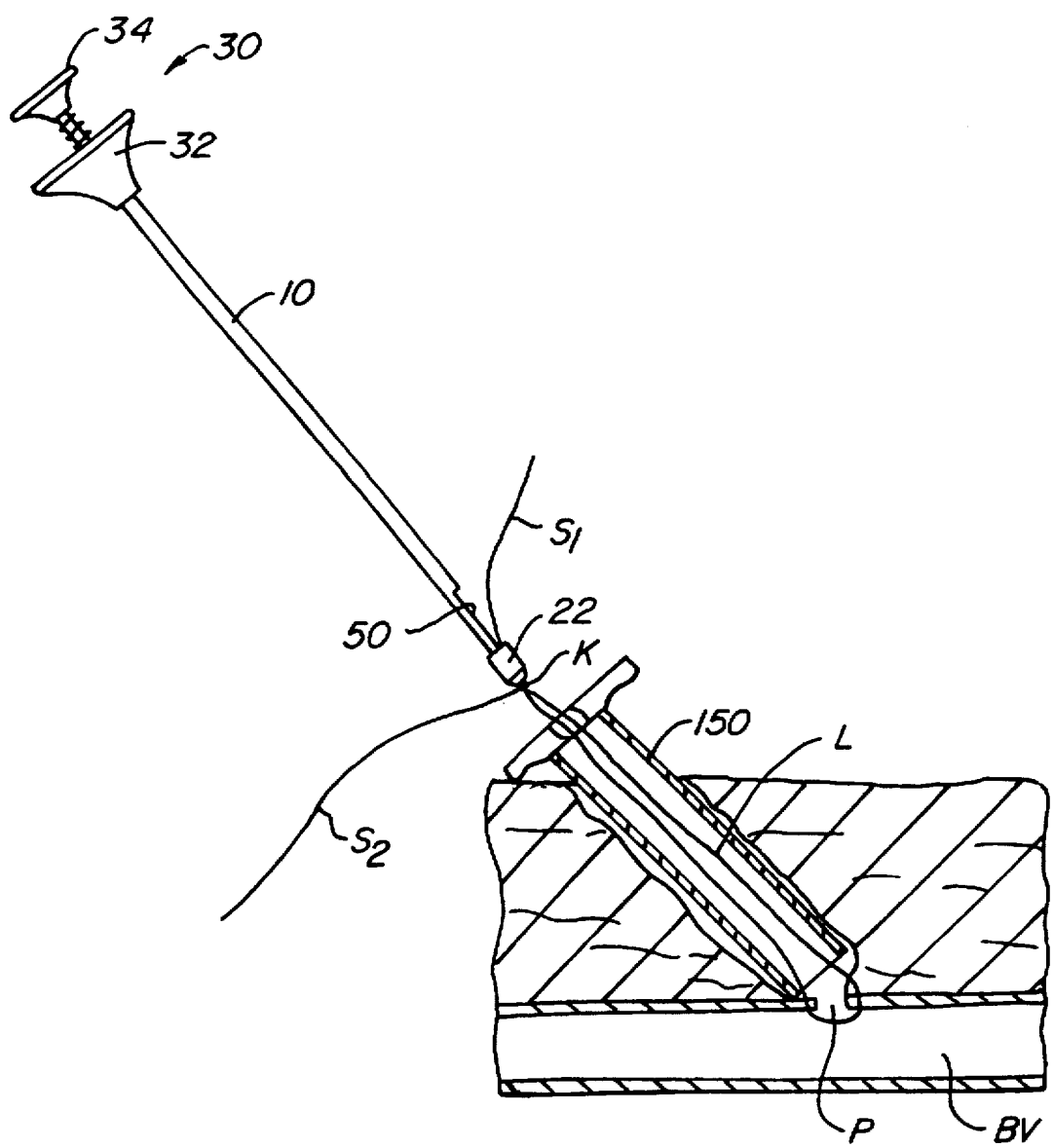
Figure 7C:
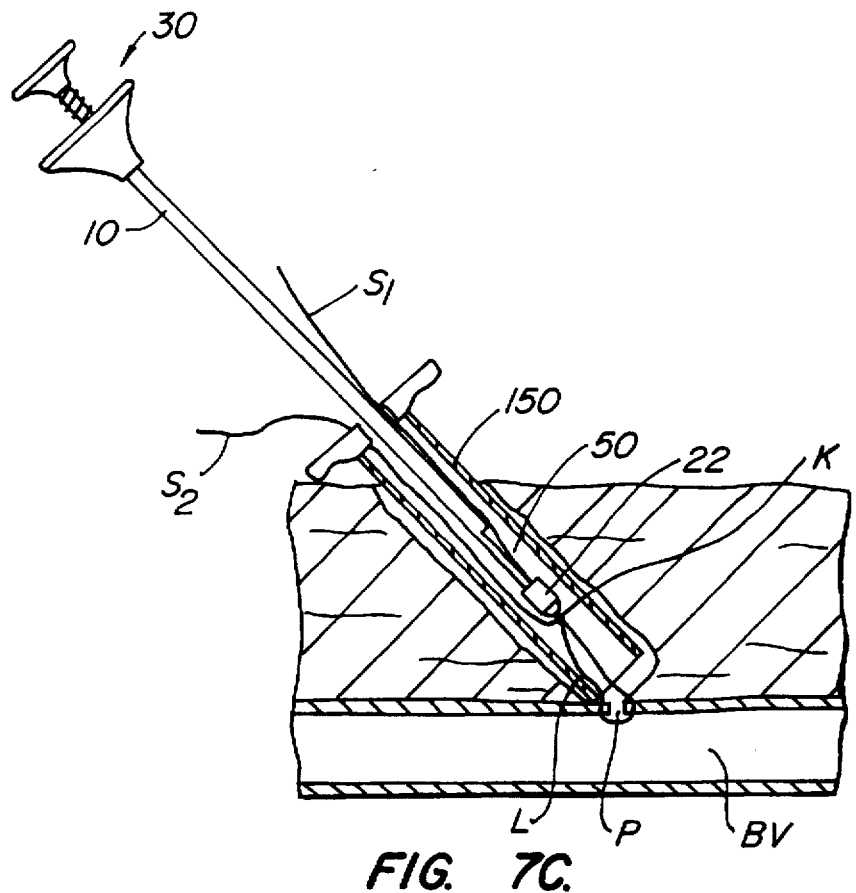
Figure 7D:
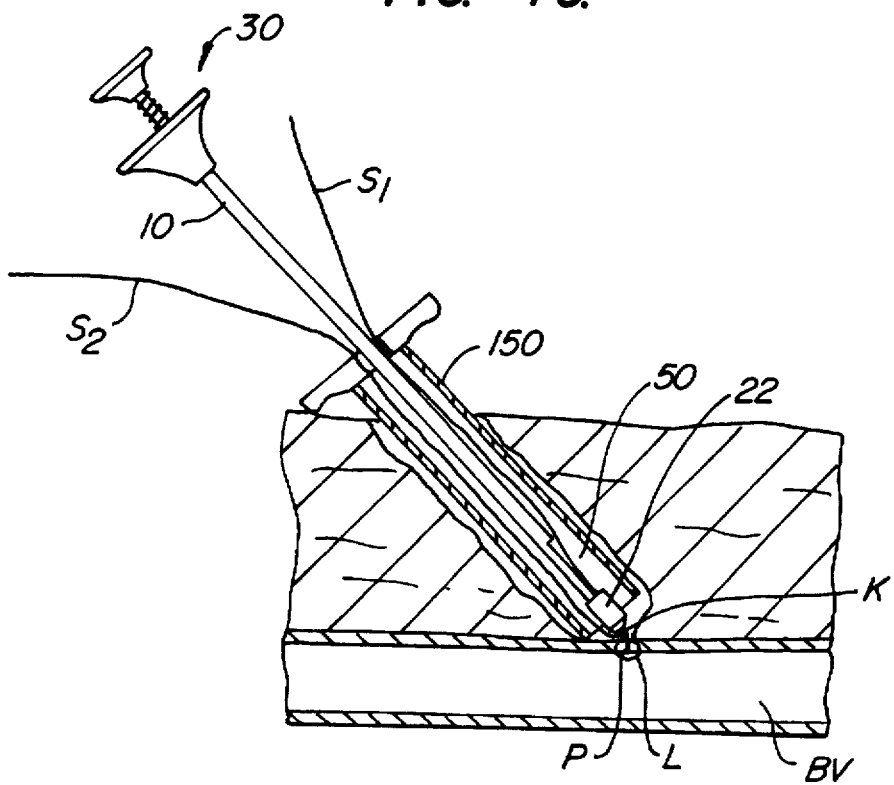
Figure 7E:
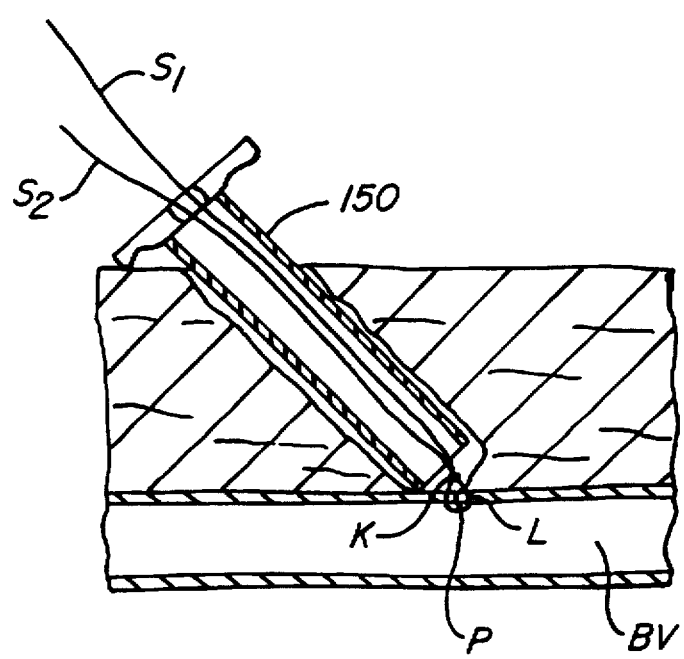

After the first free suture end S1 is captured, as illustrated in FIG. 7B, the device 10 is advanced into the lumen of sheath 150 toward the puncture P in blood vessel BV, as illustrated in FIG. 7C. The device is further advanced until the fitting 22 pushes the knot K directly over the adventitial surface of the blood vessel BV, as illustrated in FIG. 7D. The knot K can then be tightened, typically by pulling on both free ends S1 and S2, and the device 10 can then be withdrawn from the sheath 150 and released from the suture end S1, as illustrated in FIG. 7E. The free ends of the suture can then be trimmed a short distance over the knot, and the sheath 150 removed and the percutaneous tissue tract bandaged. Optionally, additional knot throws will be tied and advanced over the free suture and S1 using the knot pusher 10.

Although the foregoing invention has been described in some detail by way of illustration and example, for purposes of clarity of understanding, it will be obvious that certain changes and modifications may be practiced within the scope of the appended claims.

What is claimed is:

1. A knot pusher comprising:

a shaft having a proximal end and a distal end and an axis therebetween, the shaft having a side opening disposed proximally of the distal end;

a fitting on the distal end of the shaft, said fitting having a slot extending from the side opening to the distal end of the fitting, the slot at a different radial position than a portion of the opening;

a member having a proximal end and a distal end mounted on the shaft to move axially between a first position and a second position, the member in the first position radially blocking the slot while leaving an open passage from the distal end of the fitting to the portion of the side opening, the slot providing a radial opening to the open passage when the member is in the second position.

2. A knot pusher as claimed in claim 1, wherein the member is biased toward the first position.

3. A knot pusher as claimed in claim 1, wherein the shaft comprises a tube and the member comprises a rod disposed within the tube, the rod having an axial notch defining an axially oriented wall which blocks the slot when the member is in the first position, the rod being axially slidable without rotation relative to the tube between the first position and the second position.

4. A knot pusher comprising:

a tubular shaft having a proximal end and a distal end and an axis therebetween, the shaft having a side opening proximal of the distal end;

a fitting on the distal end of the shaft, said fitting having a radial slot in communication with the side opening so that the slot and the side opening are adapted to radially receive a length of suture;

a member having a proximal end and a distal end mounted on the shaft to slide axially between a first position that closes the slot, the slot and member adapted to radially capture the length of suture and allow the captured length of suture to slide axially when the member is in the first position, and a second position that opens the slot to allow the length of suture to enter and leave the slot radially; and a handle actuator assembly disposed at the proximal end of the shaft for moving the member between said first position and said second position with one hand;

wherein the distal end of the shaft, the fitting, and the distal end of the member are insertable into the patient body through an introduction sheath while the member remains in the first position;

wherein the member is a rod slidably received in a lumen of the shaft, wherein a distal end of the rod is shaped to close a portion of the slot when the rod is in a first axial position and to open the portion of the slot when the rod is in a second axial position, the rod angularly aligned with the slot throughout movement between the first and second positions.

5. A knot pusher as in claim 4, wherein the shaft has a length in the range from 5 cm to 40 cm and a diameter less than 10 mm.

6. A knot pusher as in claim 5, wherein the fitting is cylindrical having a length in the range from 3 mm to 10 mm and a diameter in the range from 2 mm to 10 mm.

7. A knot pusher as in claim 4, wherein the fitting is formed in the shaft as an integral component.

8. A knot pusher as in claim 4, wherein the radial slot is flared open over at least a radially outward portion thereof to facilitate capture of suture in the slot.

9. A knot pusher as in claim 4, wherein the handle actuator assembly comprises a finger grip attached at the proximal end of the rod member, a thumb depressor attached at the proximal end of the shaft, and a spring maintained under compression between the finger grip and the thumb depressor, wherein depression of the thumb depressor toward the finger grip opens the radially outward portion of the slot.

10. A knot pusher as in claim 4, wherein the handle actuator assembly comprises a tubular handle casing having an open interior or chamber and an axial slot attached to the proximal end of the shaft, a slider slidably received within the open interior chamber, a thumb knob attached to the slider and extending through the slot, and a spring maintained under compression between the slider and the handle casing to distally urge the slider, wherein proximal retraction of the thumb knob relative to the handle casing opens the radially outward portion of the slot.

11. A knot pusher as in claim 4, wherein the handle actuator assembly comprises a first knob attached to the proximal end of the shaft and a second knob attached to the rod, wherein relative rotation of the first and second knobs opens and closes the slot.

12. A knot pusher as in claim 4, further comprising an anchor adjacent to the handle, the anchor permitting temporary attachment of the length of suture.

13. An improved knot pusher of the type including a shaft having a proximal end and a distal end, wherein the distal end engages and advances a slidable knot formed on a free suture end, wherein the improvement comprises means at the distal end of the shaft for selectively capturing and releasing the suture end, the selective capturing and releasing means being biased toward a first position wherein the suture is captured so that the suture will not be inadvertently lost as the knot is advanced, the selective capturing and releasing means adapted to allow the captured suture to slide through the selective capturing and releasing means to advance the knot along the suture, and a handle actuator assembly at the proximal end of the shaft for actuating the selective capturing and releasing means, the handle allowing one-handed extracorporal actuation of the selective capturing and releasing means and one-handed manipulation of the knot pusher relative to the suture to advance the knot.

14. An improved knot pusher as in claim 13, wherein the selective capturing and releasing means comprises a member which is mounted to axially translate within the shaft to move between the first position wherein the suture is captured and a second position wherein the suture is released.

15. An improved knot pusher as in claim 9, further comprising an anchor adjacent to the handle, the anchor adapted for temporary attachment of the length of suture.

16. An improved knot pusher of the type including a shaft having a proximal end and a distal end, wherein the distal end engages and advances a slidable knot formed on a free suture end, wherein the improvement comprises means at the distal end of the shaft for selectively capturing and releasing the suture end, the selective capturing and releasing means being biased toward a first position wherein the suture is captured so that the suture will not be inadvertently lost as the knot is advanced, and a handle actuator assembly at the proximal end of the shaft for actuating the selective capturing and releasing means, the handle allowing one-handed extracorporal actuation of the selective capturing and releasing means and one-handed manipulation of the knot pusher relative to the suture to advance the knot, wherein the selective capturing and releasing means comprises a member which is rotatably mounted within the shaft to move between a first position wherein the suture is captured and a second position wherein the suture is released.

17. A method for closing a suture loop having two free ends and a knot disposed on one of said free ends, said method comprising:

tensioning said one free end with one hand while the loop is anchored in tissue;

holding a shaft in the other hand, said shaft having a slot at a distal end, the slot being biased to close;

restraining the biased slot open and manipulating the shaft with said other hand while holding and tensioning said one free end of the suture with said one hand in order to capture said one free end in said slot at the distal end of said shaft while the distal end of the shaft is outside a patient body;

allowing the biased slot to close with said other hand while continuing to hold the suture with the one hand to prevent release of the free end, the closing of said slot performed while the distal end of the shaft remains outside the patient body;

advancing the distal end of the shaft over said one free end with said other hand toward the tissue to advance the knot and close the suture loop while continuing to hold said one free end of the suture with said one hand; and releasing the free end from the slot.

18. A method as in claim 17, wherein the advancing step comprises advancing the distal end through a tissue tract toward suture anchored in a blood vessel wall.

19. A method as in claim 18, wherein the advancing step comprises advancing the distal end over the free end of suture while said free end extends outward through a sheath disposed in the tissue tract.

20. A method as in claim 17, wherein the advancing step comprises advancing a square knot.

21. A method as in claim 17, wherein tensioning said one free end comprises grasping the free end in one hand.

22. A method as in claim 17, further comprising tying and advancing additional knot throws over the first knot which had been advanced.

23. A method as in claim 17, further comprising temporarily attaching said one of said two free ends to the shaft.

* * * * *